「United States Patent [19]

Mantovani et al.

[11] Patent Number: 5,116,617
[45] Date of Patent: May 26, 1992

[54] PHARMACEUTICAL COMPOSITION FOR TOPICAL USE IN THE TREATMENT OF THE CAPILLARY FRAGILITY

[75] Inventors: Marisa Mantovani, Villa Guardia; Roberto Porta, Cernobbio; Giuseppe Prino, Milan, all of Italy

[73] Assignee: Crinos Industria Farmacobiologica S.p.A., Villa Guardia, Italy

[21] Appl. No.: 568,126

[22] Filed: Aug. 16, 1990

[30] Foreign Application Priority Data

Sep. 7, 1989 [IT] Italy ................. 21651 A/89

[51] Int. Cl.$^5$ .................. A61K 9/06; A61K 31/33
[52] U.S. Cl. ......................... 424/401; 514/44; 514/822; 514/969
[58] Field of Search ............ 514/44; 536/24; 424/401

[56] References Cited

U.S. PATENT DOCUMENTS

| | | | |
|---|---|---|---|
| 3,770,720 | 11/1973 | Butti | 536/74 |
| 3,829,567 | 8/1974 | Butti et al. | 536/24 |
| 4,649,134 | 3/1987 | Butti | 514/44 |
| 4,693,995 | 6/1987 | Prin et al. | 514/44 |

FOREIGN PATENT DOCUMENTS 0137543 9/1983 European Pat. Off. .
3505359 2/1984 Fed. Rep. of Germany ........ 514/44

OTHER PUBLICATIONS

Dorland's Illustrated Medical Dictionary, (26th ed. 1991), pp. 499 and 527.
Harrison's Principles of Internal Medicine, (11th ed. 1987) pp. 1482–1483.
The Merck Index, (10th ed. 1983), p. 1226.
Goodman and Gilman's The Pharmacological Basis of Therapeutics, (8th ed. 1990), pp. 1322–1325.
"Today's Drugs—Vitamin P", British Medical Journal, Jan. 25, 1969, pp. 235–237.

Primary Examiner—Thurman K. Page
Assistant Examiner—Raj Bawa
Attorney, Agent, or Firm—Nikaido, Marmelstein, Murray & Oram

[57] ABSTRACT

Pharmaecutical composition for topical use containing Defibrotide have been found effective in the therapy of local pathologies characterized by a reduced resistance of the blood capillary vessels.

3 Claims, No Drawings

PHARMACEUTICAL COMPOSITION FOR TOPICAL USE IN THE TREATMENT OF THE CAPILLARY FRAGILITY

Defibrotide (D.C.I., list 21, Chronique O.M.S. 35,5 suppl. 4, 1981 and Chronique O.M.S. 1 4, 1987) is a polydeoxyribonucleotide extracted from animal organs, mainly bovine lung.

This substance is a drug endowed with a fibrinolytic (U.S. Pat. No. 3,829,567) and antithrombotical activity.

Several patents relating to different therapeutical uses of Defibrotide were applied for (and granted) in recent years, such as for example the use in the treatment of acute renal insufficiency (U.S. Pat. No. 4,649,139), in the acute myocardial ischemia (U.S. Pat. No. 4,693,895) and in the peripheral artheriopaties of III and IV phases (EP-A-84201287.4).

The object of the present invention is the use of Defibrotide, as carried out through the topical administration of corresponding pharmaceutical formulations in which it is contained, for local pathologies, characterized by a reduced resistance of the blood capillary vessels.

The novel activity has been demonstrated in the experimental animal (rat), in which the capillary fragility was induced by means of a diet lacking bioflavonoids (vitamin P complex), as prepared according to Charlier (Charlier et al, "Fragilité vasculaire", Arch. Int. Phys. et Biochimie 1983), and commercially available.

The rats fed with this diet were on the whole 156, divided into 7 groups, as indicated in Table I, wherein also the pharmaceutical preparation used for the topical administration to each group is stated.

From the same Table it is seen that 2 groups (F and G), among those taken into consideration, have been treated with pharmaceutical preparations already available on the market, which are currently used in the local therapy of the aforesaid pathologies.

In Table II the compositions and therapeutical indications of these preparations are reported.

Example 1 detailedly illustrates the composition of the formulations for topical use containing Defibrotide which have been used in these experiments.

The experimental study has been completed by including also a control group, consisting of 24 rats, which were fed with a normal diet (MIL Morini diet).

The feeding with the Charlier diet has been extended to 28 days on the whole. On the 21st day the animals were subjected to a test aiming to assess whether the reduction of the capillary resistance induced by the Charlier diet was homogeneous throughout the several groups of rats to be subsequently subjected to the topical treatment.

The assessment of the capillary resistance has been carried out according to the technique of Lavollay (J. Lavollay et al. "Problems posed by activity of certain flavonoids on vascular resistance". Pharmacology of plant phenolics, Symposium Oxford 1958, Proceedings pag. 103-122 Publ. 1959). Shortly stated, the skin of the back lombar area was carefully shaved and slightly oiled with vaseline oil. The zone useful for the measurement corresponded to an area of about $2 \times 1.5$ cm, extending as to the length to the last ribs and delimiting as to the width the paravertebral bands. The animals were subjected to a slight anaesthesia and then to the back area, as previously individuated, there was applied the instrument for the determination of the capillary resistance, essentially consisting of a sucker connected with a vacuum pump (petecchiometro, Baldinelli Milano). This apparatus thus permits the value of the depression, as expressed in mm Hg, to be determined, which is capable of causing the breaking of the surface capillary vessels.

By means of the aforesaid technique, it has been assessed that the animals fed with the Charlier diet (groups from A to G) had, with respect to the animals of the control group, a significantly reduced capillary resistance; such a reduction was statistically homogeneous throughout the several groups (Table III).

The treatment by topical route was started on the 22nd day and prosecuted for the next seven days. The skin area of the animals, to which the formulations referred to in the Table I were applied, was the back lombar one, in which previously the area was individuated on which the determination of the capillary resistance was carried out by the instrument, as above-described. The administrations were repeated three times a day, by topically applying each time 0.2 ml of each pharmaceutical formulation or 0.2 ml of physiological solution in the rats of the control group and of the group A of Table I.

At the end of the treatment period the capillary resistance has again been determined by the above-illustrated technique. The results are reported in Table III.

TABLE I

| Groups fed with the Charlier diet, number of animals for each group and related topical treatment. | | |
| --- | --- | --- |
| Groups | No. of Animals | Topical Treatment |
| A | 26 | Physiological solution |
| B | 25 | Placebo gel* |
| C | 23 | 1.25% Defibrotide gel (example 1) |
| D | 23 | 2.5% Defibrotide gel (example 1) |
| E | 25 | 5.0% Defibrotide gel (example 1) |
| F | 23 | Commercially available cream (Table II) |
| G | 11 | Commercially available gel (Table II) |

*The composition of the gel is the same as that of example 1, apart from the active principle.

TABLE II

| Compositions and therapeutical indications of the pharmaceutical formulations respectively used for the groups F and G of the previous Table I. | | |
| --- | --- | --- |
| | Commercially Available Cream | Commercially Available Gel |
| Composition: | | |
| Active principles | Fibrinolysine 30 U Loomis Bovine Deoxyribonuclease 20.000 U Christensen | 0-(β-hydroxyethyl)-rutosidea g. 2 |
| Excipients: | Cream base consisting of 95% by weight of vaseline and 5% of polyethylene- | Polymerized acrylic acid mg 600, 30% sodium hydroxyde mg 600, disodium |

TABLE II-continued

Compositions and therapeutical indications of the pharmaceutical formulations respectively used for the groups F and G of the previous Table I.

| | Commercially Available Cream | Commercially Available Gel |
|---|---|---|
| | glycol | ethylenediaminotetracetate mg 50, benzalkonium chloride mg 5, distilled water balance to g 100 |
| Therapeutical indications | Ulcers induced from varicose veins, arteriosclerosis and diabetes, burns, bed-sores, wounds, cervicitis, vaginitis for the dissolution or removal of exudates and of fragments of necrotic tissues. | For the treatment of varicose veins, veneous stasis haemorrhoids, circulatory diseases, due to increased permability and fragility of the capillary vessels. |

TABLE III

Capillary resistance: average values of the determinations carried out for each group of animals (according to the method of Lavollay) on the 21st day from the beginning of the administrations to rats of the Charlier diet (before the topical treatment) and on the 28th day (after seven days of topical treatment).
The values are expressed as mm Hg.

| Groups | Determinations on the 21st day (before the topical treatment) | Determinations on the 28th day (after 7 days of topical treatment) | Increase of the capillary resistance (vs. group A) as induced from the topical treatment |
|---|---|---|---|
| Control | 315 | 315 | — |
| A | 168 | 171 | —(=100%) |
| B | 168 | 170 | 0 |
| C | 168 | 218* | +27 |
| D | 176 | 239* | +40 |
| E | 182 | 277* | +62 |
| F | 177 | 175 | +2 |
| G | 175 | 211* | +23 |

*P < 0.01 vs. group A (only diet inducing capillary fragility)

As it can be seen from Table A, the topical application of Defibrotide, as carried out through the corresponding pharmaceutical formulations containing it and by operating according to an experimental scheme which has been described above, has caused with every tested dose a statistically significant increase (P to 0.01) of the capillary resistance.

It is worthwhile to note that the gel containing the drug at the highest concentration (5%, group E) has brought the average value of the capillary resistance to values (−12%) like those detected in the controls; in the group E, as a matter of fact, the capillary resistance was higher by 62% than that of the rats fed with the Charlier diet and not topically treated (group B).

In the same Table is seen that the commercially available cream (group F) has not influenced the pathology which was experimentally induced in the animals.

It is furthermore to be noticed that the commercially available gel, containing as active principle the O-(β-hydroxyethyl)-rutosidea at a concentration of 2%, has shown the same effectiveness as the gel containing Defibrotide at a concentration of 1.25%.

The statistical analysis has demonstrated that the effect of Defibrotide, topically applied through the corresponding pharmaceutical formulations, is depending on the dose and the statistical analysis has demonstrated that the effect of Defibrotide, topically applied through the corresponding pharmaceutical formulations, is depending on the dose and that the regression which is in this way individuated is highly significant (P to 0.001).

The value of Defibrotide concentration in the corresponding pharmaceutical form by which there is obtained, owing to the topical administrations as above-described, a reduction by 50% of the value of the capillary fragility experimentally induced in the animals fed with the Charlier diet (CE50, reliability limits P=0.95) has been found to be of 3% (2.7-3.4%).

The formulations for topical use containing Defibrotide can be provided in the form of gels or creams with a concentration of active principle of between 1 and 5%, preferably 3%.

The excipients included in the aforesaid pharmaceutical forms are those usually employed and well-known to the skilled man.

There are hereinafter reported as examples, but without limiting the scope of the present invention, some compositions of pharmaceutical forms for topical use.

EXAMPLE 1

Gel Formulations

| Components | | 1.25% Defibrotide gel concentration | 2.50% Defibrotide gel concentration | 5.00% Defibrotide gel concentration |
|---|---|---|---|---|
| Defibrotide | g | 1.25 | 2.5 | 5.0 |
| Carbopol 940 | g | 2.0 | 2.0 | 2.0 |

| Components | | 1.25% Defibrotide gel concentration | 2.50% Defibrotide gel concentration | 5.00% Defibrotide gel concentration |
| --- | --- | --- | --- | --- |
| Propylene glycol | g | 4.0 | 4.0 | 4.0 |
| Benzyl alcohol | g | 1.4 | 1.4 | 1.4 |
| Isopropyl alcohol | g | 2.0 | 2.0 | 2.0 |
| EDTA | g | 0.05 | 0.05 | 0.05 |
| Methyl p-hydroxybenzoate | g | 0.03 | 0.03 | 0.03 |
| 20% sodium hydrate | g | 4.0 | 4.0 | 4.0 |
| Distilled water | g | 100 | 100 | 100 |
| Balance to pH | | 7 | 7 | 7 |

EXAMPLE 2

| A/O cream | | |
| --- | --- | --- |
| Difibrotide | g | 3 |
| Hydrogenated phospholipids | g | 1 |
| A/O Emulsifier (Deymus K) | g | 1.2 |
| Almond oil | g | 3 |
| Glycerine | g | 5 |
| Pure lanoline | g | 10 |
| Isopropyl miristate | g | 5 |
| Vaseline oil | g | 5 |
| Preservants and perfumes | | enough |
| Distilled water | g | 100 |
| Balance to | | |

EXAMPLE 3

| O/A Cream | | |
| --- | --- | --- |
| Defibrotide | g | 4 |
| Polyoxyethylenegycole stearate | g | 7 |
| Cetylstearylic alcohol | | |
| Glyceryle monostearate | g | 3 |
| Propyleneglycol | g | 5 |
| Acetoglyceride | g | 5 |
| Glycerine tricaprilate | g | 5 |
| Preservants and perfumes | | enough |
| Distilled water | g | 100 |
| Balance to | | |

We claim:

1. A method of strengthening capillaries in a human in need of such treatment, comprising topically applying a composition to the skin of said human, said composition being in the form of a gel, ointment, cream or lotion, and containing Defibrotide in an amount effective to strengthen said capillaries.

2. The method of claim 1, characterized in that the amount of Defibrotide is between 2.7 to 3.4% by weight of the composition.

3. A method of strengthening capillaries in a human in need of such treatment, comprising topically applying between 1 to 5% by weight of Defibrotide to the skin of said human to strengthen said capillaries.

* * * * *